(12) United States Patent
Minshull et al.

(10) Patent No.: US 7,322,352 B2
(45) Date of Patent: Jan. 29, 2008

(54) INHALER

(75) Inventors: Stephen John Minshull, West Malling (GB); Duncan Grant Young, London (GB); Andrew J. Ledgeway, London (GB); Simon Paul Wells, London (GB); Graham Keith Lacy, London (GB); Julian Francis R. Swan, London (GB)

(73) Assignee: Aventis Pharma Limited, West Malling (GB)

( * ) Notice: Subject to any disclaimer, the term of this patent is extended or adjusted under 35 U.S.C. 154(b) by 857 days.

(21) Appl. No.: 10/665,873

(22) Filed: Sep. 18, 2003

(65) Prior Publication Data

US 2004/0211420 A1 Oct. 28, 2004

Related U.S. Application Data

(60) Provisional application No. 60/417,534, filed on Oct. 10, 2002.

(30) Foreign Application Priority Data

Sep. 21, 2002 (GB) ................... 0222023.4

(51) Int. Cl.
*A61M 11/00* (2006.01)
(52) U.S. Cl. .................. 128/203.15; 128/205.23; 116/299
(58) Field of Classification Search ........... 128/200.24, 128/203.15, 203.23, 205.23; 116/299, 314, 116/317; 222/23, 29
See application file for complete search history.

(56) References Cited

U.S. PATENT DOCUMENTS

| 4,011,829 | A | 3/1977 | Wachsmann et al. |
|---|---|---|---|
| 4,528,933 | A | 7/1985 | Allen et al. |
| 4,565,302 | A | 1/1986 | Pfeiffer et al. |
| 5,009,338 | A | 4/1991 | Barker et al. |
| 5,176,132 | A | 1/1993 | Drought et al. |
| 5,678,538 | A | 10/1997 | Drought et al. |
| 5,687,710 | A | 11/1997 | Ambrosio et al. |
| 5,740,792 | A | 4/1998 | Ashley et al. |
| 5,829,434 | A | 11/1998 | Ambrosio et al. |
| 5,988,496 | A | 11/1999 | Bruna et al. |
| 6,076,521 | A | 6/2000 | Lindahl et al. |
| 6,182,655 | B1 | 2/2001 | Keller et al. |
| 6,240,918 | B1 | 6/2001 | Ambrosio et al. |
| 6,273,085 | B1 | 8/2001 | Eisele et al. |
| 6,484,717 | B1 | 11/2002 | Dagsland et al. |
| 6,701,917 | B2 | 3/2004 | O'Leary et al. |
| 6,752,153 | B1 | 6/2004 | Eckert et al. |
| 6,761,161 | B2 | 7/2004 | Scarrott et al. |

FOREIGN PATENT DOCUMENTS

| WO | WO 94/14492 | 7/1994 |
|---|---|---|
| WO | WO 95/34874 | 12/1995 |
| WO | WO 96/16687 | 6/1996 |
| WO | WO 97/20589 | 6/1997 |
| WO | WO 97/30743 | 8/1997 |

(Continued)

*Primary Examiner*—Steven O. Douglas
(74) *Attorney, Agent, or Firm*—Paul R. Darkes

(57) ABSTRACT

Provided herein are dry powder inhalers for the delivery of metered doses of medicament, counters associated with the inhalers for counting and displaying the number of doses administered or remaining within the inhaler, and methods of use thereof.

79 Claims, 7 Drawing Sheets

FOREIGN PATENT DOCUMENTS

| | | | | | | |
|---|---|---|---|---|---|---|
| WO | WO 98/41257 | 9/1998 | WO | WO 99/49920 | 10/1999 |
| WO | WO 98/41258 | 9/1998 | WO | WO 01/31578 | 5/2001 |
| | | | WO | WO 02/053295 | 7/2002 |

INHALER

PRIORITY CLAIM

This Application claims the benefit of U.S. Provisional Application No. 60/417,534 filed Oct. 10, 2002, which is hereby incorporated by reference herein in its entirety, and also claims priority from British Patent Application No. 0222023.4 filed Sep. 21, 2002.

FIELD OF THE INVENTION

This invention concerns dry powder inhalers for the delivery of metered doses of medicament, and counters associated with the inhalers for counting and displaying the number of doses administered or remaining within the inhaler.

BACKGROUND OF THE INVENTION

Oral delivery of medicaments to treat disorders such as asthma, emphysema and chronic bronchitis has been, for many years, reliably and effectively accomplished through the use of pressurized metered dose inhalers (PMDIs). Such inhalers provide a stream of atomized medicament inhaled directly into the affected air passageways and lungs to afford rapid relief from the symptoms of such disorders.

As an alternative to PMDIs, dry powder inhalers (DPIs) have received considerable attention because of their propellant-free composition and their relative ease of operation compared to PMDIs. DPIs can be used for oral and nasal administration and may be presented with the drug formulation pre-metered as capsules (unit-dose inhaler), blisters and cartridges (multi-unit dose inhaler) or as bulk material in a reservoir (multi-dose inhalers).

A necessary design feature of PMDIs and multi-dose DPIs is that they contain more formulation than strictly required to expel the labeled number of actuations/doses. A potential problem which may be particularly acute for PMDIs is dose inconsistency beyond the labeled number of actuations/doses. A patient unknowingly using a PMDI or multi-dose DPI beyond the recommended number of doses may risk not receiving the correct drug dose with possibly dangerous consequences.

To avoid this problem, it is desirable to include a counter integrally with the inhaler to count and display to the user the number of doses remaining within the inhaler. This will allow the user sufficient warning as to when the inhaler is running low and should, therefore, be replaced so as to avoid the potential for sub-therapeutic dose administration. The counter should be simple in design, reliable in operation and easy to read and interpret.

SUMMARY AND OBJECTS OF THE INVENTION

The invention concerns a dry powder inhaler for administering a metered dose of a medicament to a user. The inhaler comprises a reservoir holding the medicament and an air channel assembly engaged with and movable relatively to the reservoir for receiving the dose of medicament upon the relative motion. The medicament is administered when the user draws a breath through the air channel assembly; the medicament, in powdered form, being entrained in the air drawn through the air channel assembly and into the user's air passageways.

The inhaler also comprises a counter for counting the number of doses dispensed from the reservoir or the number of doses that can still be delivered before the device is considered empty. The counter comprises a first indicator member which moves one increment in response to the motion of the air channel assembly relative to the reservoir. The increment of movement corresponds to each dose dispensed from the reservoir. The counter also has a second indicator member which moves intermittently in response to motion of the first indicator member. Both indicator members have indicia thereon for displaying the number of doses dispensed from the reservoir or the number of doses that can still be delivered before the device is considered empty. A rotatory intermittent drive transfer mechanism is positioned between, and engaged with, the first and second indicator members. In operation, the first indicator member drives the rotatory intermittent drive transfer mechanism and the rotatory intermittent drive transfer mechanism drives the second indicator member intermittently upon motion of the first indicator member. Preferably, the first indicator member is a unit wheel. Preferably, the second indicator member moves one increment for every ten increments of the unit wheel (hereinafter a "tens" wheel), and the indicia thereon represent tens of doses, whereas the indicia on the unit wheel represent unit doses. Also, it is foreseeable that the inhaler comprise a third, and optionally fourth, indicator member. The third indicator member can move one increment for every 100 increments of the tens wheel (hereinafter a "hundreds" wheel), and the indicia thereon represent hundreds of doses. The fourth indicator member can move one increment for every 1000 increments of the hundreds wheel (hereinafter a "thousands" wheel), and the indicia thereon represent thousands of doses.

Preferably, the reservoir is arranged circumferentially around a central axis and the air channel assembly is positioned coaxially with the reservoir and rotatably movable about the central axis relatively thereto. The first and second indicator members are also preferably positioned coaxially with the reservoir and rotatably movable about the central axis for counting the doses dispensed from the reservoir or the number of doses that can still be delivered before the device is considered empty.

The unit wheel has a first surface on which the counting indicia representing unit doses appear, the first surface facing radially outwardly from the central axis. The tens wheel has a second surface on which the indicia representing tens of doses appear, the second surface being transparent and facing radially outwardly from the central axis. The unit wheel is preferably nested within the tens wheel and the indicia on the unit wheel juxtapose with the indicia on the tens wheel and are visible through the transparent surface of the tens wheel to display the number of the doses dispensed from the reservoir or the number of doses that can still be delivered before the device is considered empty.

As noted above, the unit and tens wheels are connected by a rotatory intermittent drive transfer mechanism which imparts intermittent motion to the tens wheel upon motion of the unit wheel. Preferably, the rotatory intermittent drive transfer mechanism comprises a slave wheel rotatable about an offset axis offset from the central axis and substantially parallel thereto. The slave wheel has a drive transfer wheel on one face and a gear on the opposite face. Preferably, the unit wheel has a foot extending therefrom for engaging the drive transfer wheel, and the tens wheel has gear teeth arranged around its interior surface circumference for meshing with the gear on the opposite face of the slave wheel. Upon a predetermined number of incremental movements of the unit wheel (preferably 10), the foot on the unit wheel engages with the drive transfer wheel and causes the slave wheel to rotate, whereupon the gear teeth on the slave wheel engage and rotate the tens wheel one increment. It is preferred that the gear and drive transfer wheel are situated in the interior circumference, so that the drive transfer mechanism is able to drive the unit and tens wheel in the same direction. However, it is also foreseeable that by using interior and exterior drive transfer wheels and gears, the drive transfer mechanism is able to drive the unit and tens wheel in the opposite direction to each other. Also, it is foreseeable that by changing the gear ratio, the total number of doses that can be displayed by the counter can also be changed.

The slave wheel may incrementally rotate the tens wheel intermittently in response to rotation of the unit wheel in accordance with the following preferred embodiment. Thus, the unit wheel has an inwardly facing circumferential surface with a notch therein. The foot, which extends from the unit wheel, is positioned adjacent to the notch. The drive transfer wheel, positioned on a face of the slave wheel facing the unit wheel, has a plurality of receptacles spaced circumferentially therearound, each for receiving the foot on the unit wheel. A rotation-preventing feature is embodied in a plurality of outwardly extending lobes positioned between the drive transfer wheel and the gear on the slave wheel. Each of the lobes is aligned with a respective receptacle on the drive transfer wheel, one or more of the lobes engaging the inner circumferential surface of the unit wheel as the unit wheel rotates, thereby preventing inadvertent rotation of the slave wheel and, thus, the tens wheel. One lobe of the slave wheel is received within the notch in the inner circumferential surface of the unit wheel when the foot of the unit wheel engages one of the receptacles on the drive transfer wheel aligned with the lobe to rotate the slave wheel. The notch provides clearance between the lobe and the inner circumferential surface of the unit wheel, allowing the slave wheel to incrementally rotate, thereby rotating the tens wheel. Another of the lobes then engages the inner circumferential surface of the unit wheel upon incremental rotation of the slave wheel, thereby again preventing rotation of the slave wheel until the foot on the unit wheel again engages the next one of the receptacles, aligned with the next lobe, on the drive transfer wheel.

It is an object of the invention to provide an inhaler with a counter for counting the doses dispensed from the inhaler or the number of doses that can still be delivered before the device is considered empty.

It is a further object of the invention to provide a counter actuated by rotary motion of a component of the inhaler.

It is another object of the invention to provide a counter having a first indicator member (e.g. a unit wheel) which intermittently drives a second indicator member (e.g. a tens wheel) through a rotatory intermittent drive transfer mechanism.

It is yet another object of the invention to provide a counter, wherein the first indicator member (e.g. a unit wheel) is coaxially nested within the second indicator member (e.g. a tens wheel).

It is still another object of the invention to provide a counter, wherein the rotatory intermittent drive transfer mechanism provides a locking feature preventing undesired motion of the tens wheel.

It is again another object of the invention to provide a rotatory intermittent drive transfer mechanism comprising a slave wheel with a drive transfer wheel on one face and a gear on the opposite face.

It is appreciated that certain features of the invention, which are, for clarity, described in the context of separate embodiments, may also be provided in combination in a single embodiment. Also, various features of the invention which are, for brevity, described in the context of a single embodiment, may also be provided separately or in any suitable sub-combination.

These and other objects and advantages of the invention will become apparent upon consideration of the following drawings and detailed description of preferred embodiments of the invention.

DETAILED DESCRIPTION OF THE PREFERRED EMBODIMENTS

By way of example only, a geneva mechanism, which intermittently transfers the drive from one element to another via geneva wheel, is described below, it being understood that any intermittent drive transfer mechanism incorporating an intermittent drive transfer wheel, works essentially the same way and could be used in the claimed invention.

Figure 1:
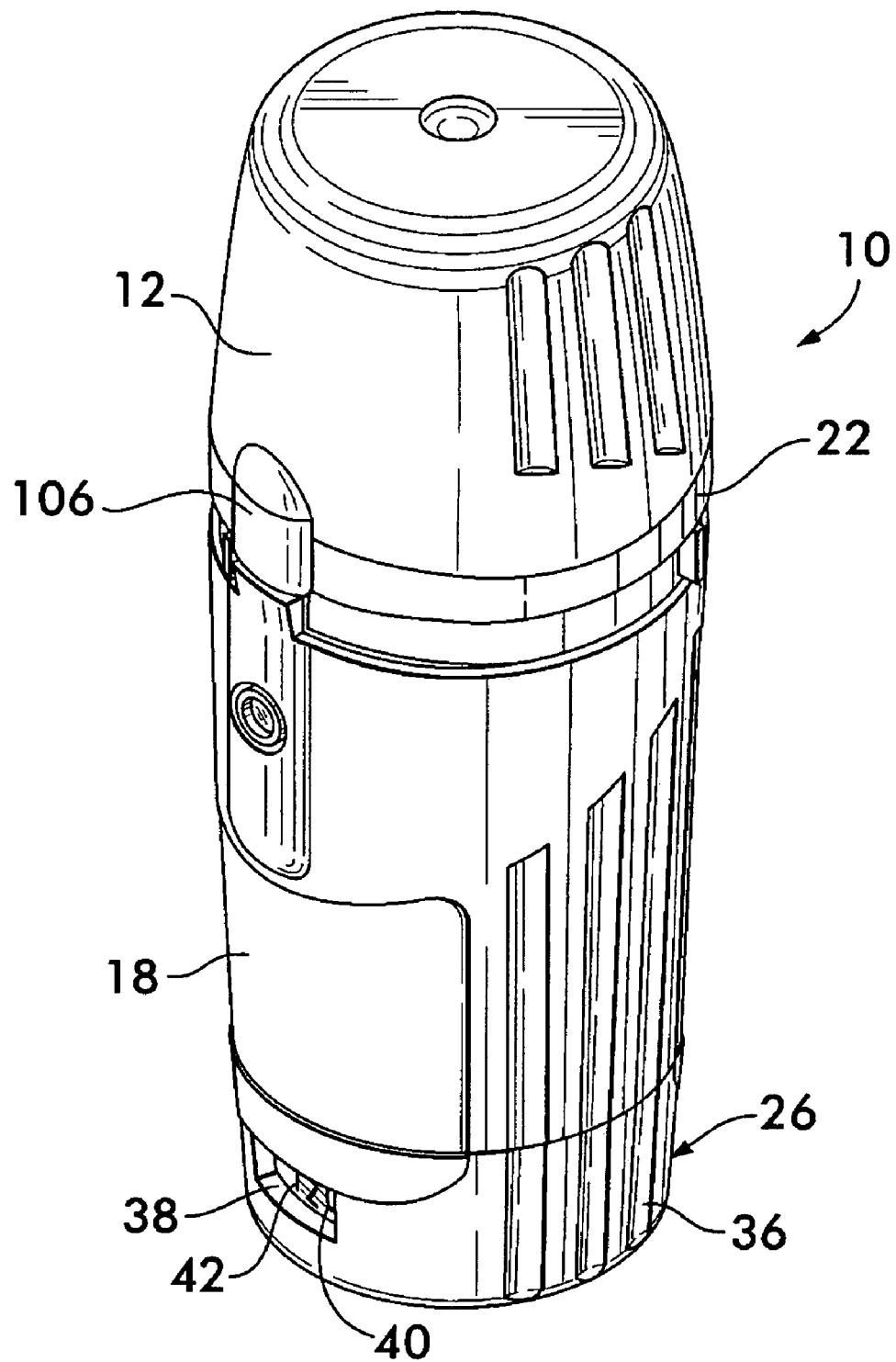
FIG. 1 is a perspective view of the inhaler according to the invention.
Figure 2:
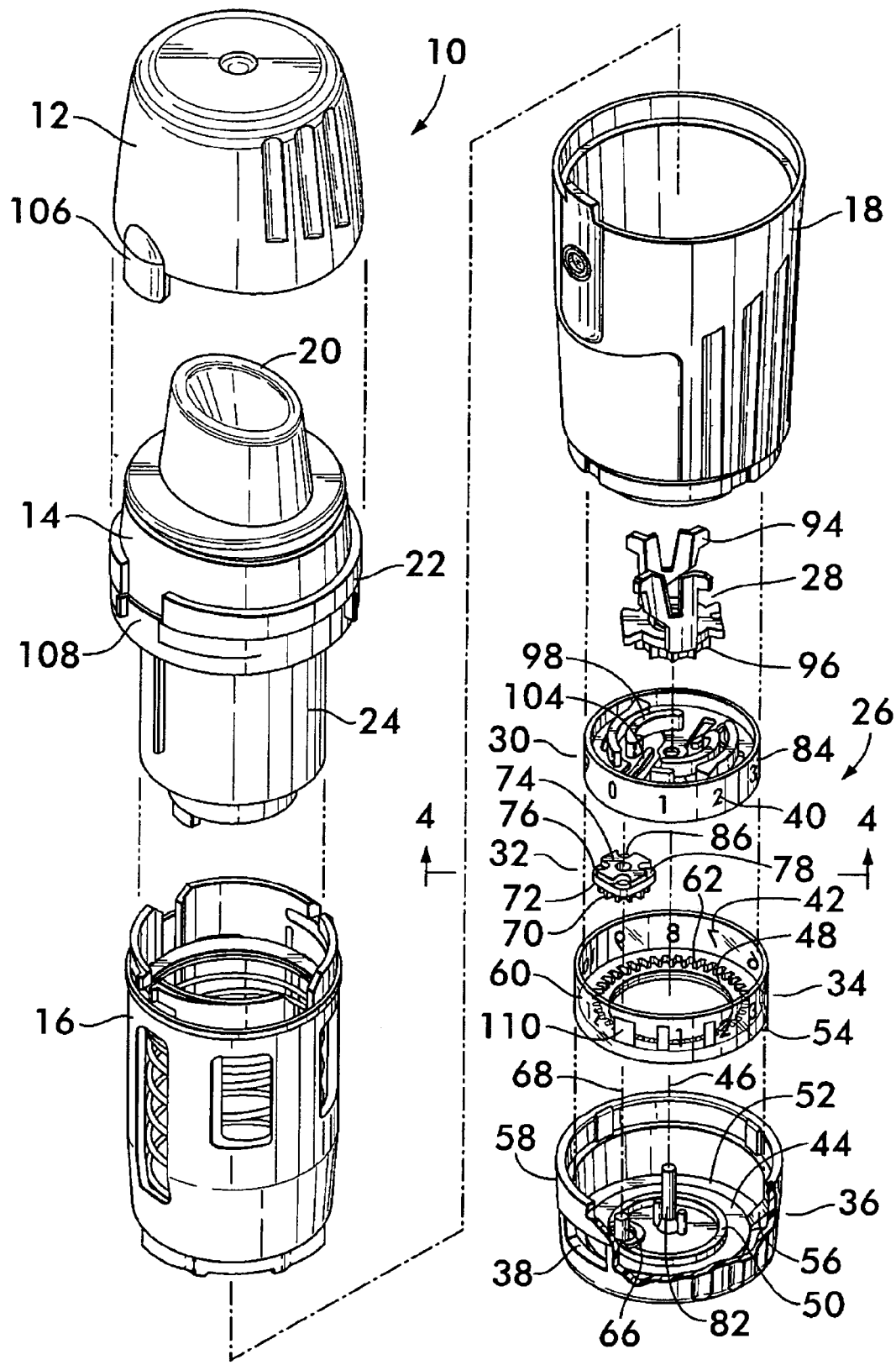
FIG. 2 is an exploded perspective view of the inhaler shown in FIG. 1.

FIG. 1 is a perspective view of a preferred embodiment of an inhaler 10 according to the invention. FIG. 2 is an exploded view of the inhaler 10 shown in FIG. 1. Moving downwardly and from left to right in FIG. 2, the inhaler comprises a dust cap 12, an air channel assembly 14, a medicament reservoir 16 for holding a powdered medicament (not shown) and a barrel 18. The air channel assembly 14 comprises a mouthpiece 20, a collar 22, a reservoir 16, and a drive sub-assembly 112. Drive sub-assembly 112 fits coaxially within barrel 18, and the reservoir 16 of air channel assembly 14 fits coaxially within the drive sub-assembly 112. Collar 22 and mouthpiece 20 on the end of the air channel assembly 14 extend outwardly from the reservoir 16 and barrel 18 to engage the lips of a user as described below.

A counter 26 is mounted onto the inhaler 10 on the end of barrel 18 opposite the dust cap 12. Counter 26 comprises a coupling 28, a unit wheel 30, a slave wheel 32, a tens wheel 34 and a cover 36 in which the unit wheel 30, slave wheel 32 and tens wheel 34 are rotatably mounted. Cover 36 has a window 38 therein through which indicia 40 and 42, printed on the unit and tens wheels respectively, may be viewed, indicating the number of doses that can still be delivered before the medicament reservoir 16 is considered empty or the number of doses dispensed therefrom.

As shown in detail in FIG. 2, cover 36 of counter 26 has a bottom 44 which supports the tens wheel 34 for rotational motion about a central axis 46. Tens wheel 34 has an inwardly extending flange 48 which is sized to surround and engage a raised boss 50 positioned on the bottom 44 concentric with the central axis 46 (see also FIGS. 4 and 4A). Cooperation between the flange 48 and the boss 50 keeps the tens wheel 34 concentric within the cover 36 and allows guided rotation of the tens wheel about the central axis 46. Bottom 44 also has a circular groove 52 positioned concentric with the central axis. The groove 52 is sized to accept a tab 54, best shown in FIG. 3. The tab 54 extends downwardly from the tens wheel 34 and tracks within the groove 52 as the tens wheel rotates about central axis 46. As shown in FIG. 2, a stop block 56 is positioned within the groove 52. When the tens wheel 34 has rotated such that the last of the series of indicia has been displayed in the window 38, the stop block 56 engages the tab 54 to halt its rotation and thereby preventing the counter from resetting itself after it has counted down to zero and thus give a false reading of the number of doses remaining in the inhaler. Also, when incrementing the counter it is foreseeable that the stop block's 56 ability to engage the tab 54 to halt its rotation would also prevent the counter from resetting itself when the last of the series of indicia has been displayed in the window 38.

As shown in FIGS. 2 through 4A, an outwardly facing sidewall 58 on the cover 36 extends circumferentially around the bottom 44 and is attached to the end of barrel 18 to enclose the counter 26. The cover 36 is mounted onto the barrel 18 by means of a snap fit (not shown). Window 38 is positioned in sidewall 58, allowing viewing of indicia 40 and 42. Indicia 42 are positioned on a radially outwardly facing side surface 60 extending circumferentially around the tens wheel 34. Alternatively, the indicia 42 can be positioned on the radially inwardly facing side surface extending circumferentially around the tens wheel 34. Side surface 60 is positioned concentric with central axis 46 and is adjacent to sidewall 58. Indicia 42 thereon are positioned so as to align with and be visible through the window 38 as the tens wheel rotates within the cover 36. The tens wheel 34 is a decimal wheel showing tens of doses that can still be delivered before the device is considered empty, and thus, the indicia 42 thereon are positioned and spaced apart on the side surface 60 to align to the left side of the window 38, leaving room in the window for indicia 40 on the unit wheel 30 to be displayed through window 38 to the right of the indicia 42 on the tens wheel 34 to properly indicate the unit number of doses that can still be delivered before the device is considered empty.

Figure 3:
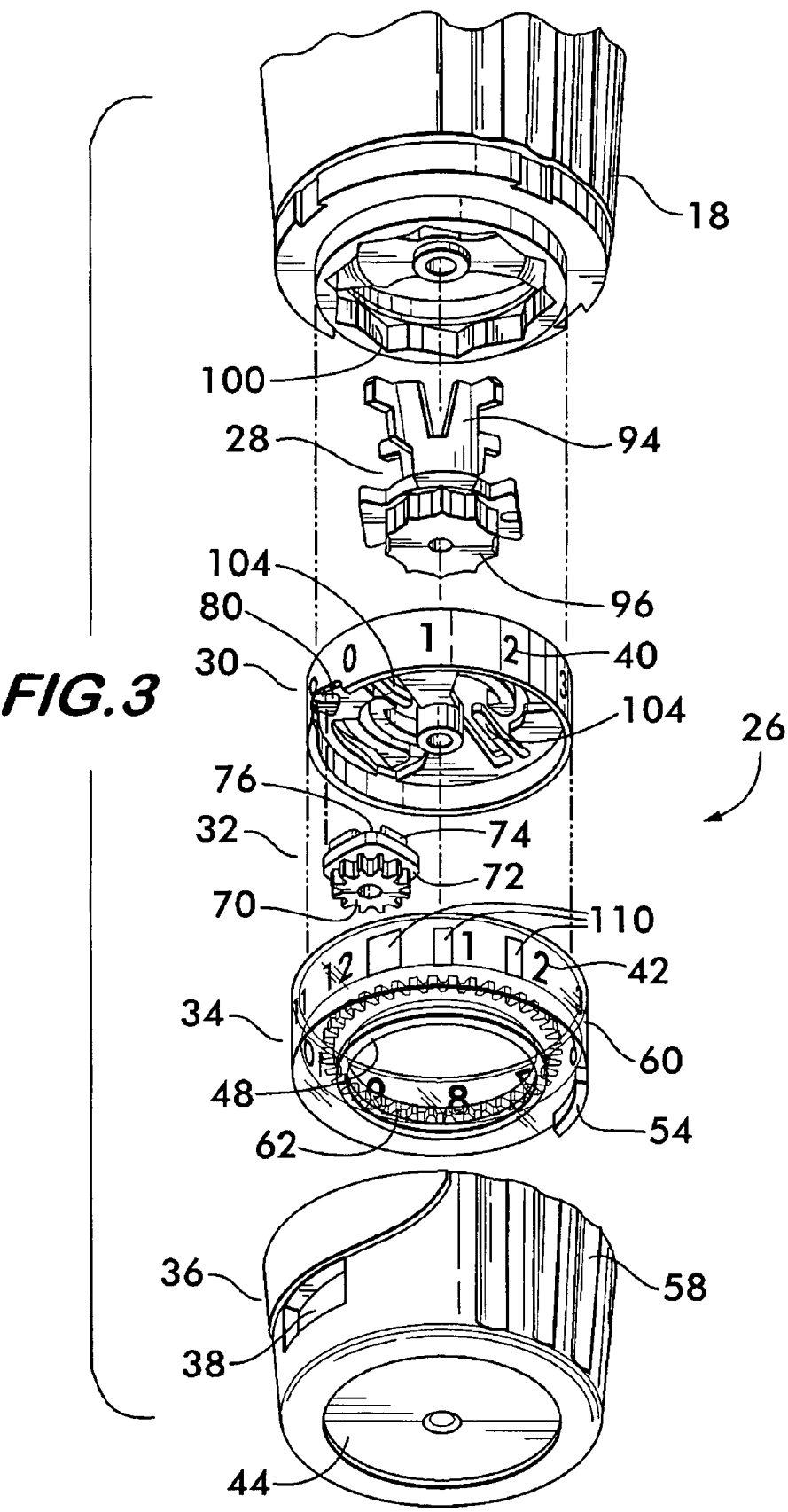
FIG. 3 is a partial exploded perspective view showing the counter for the inhaler.
Figure 6:
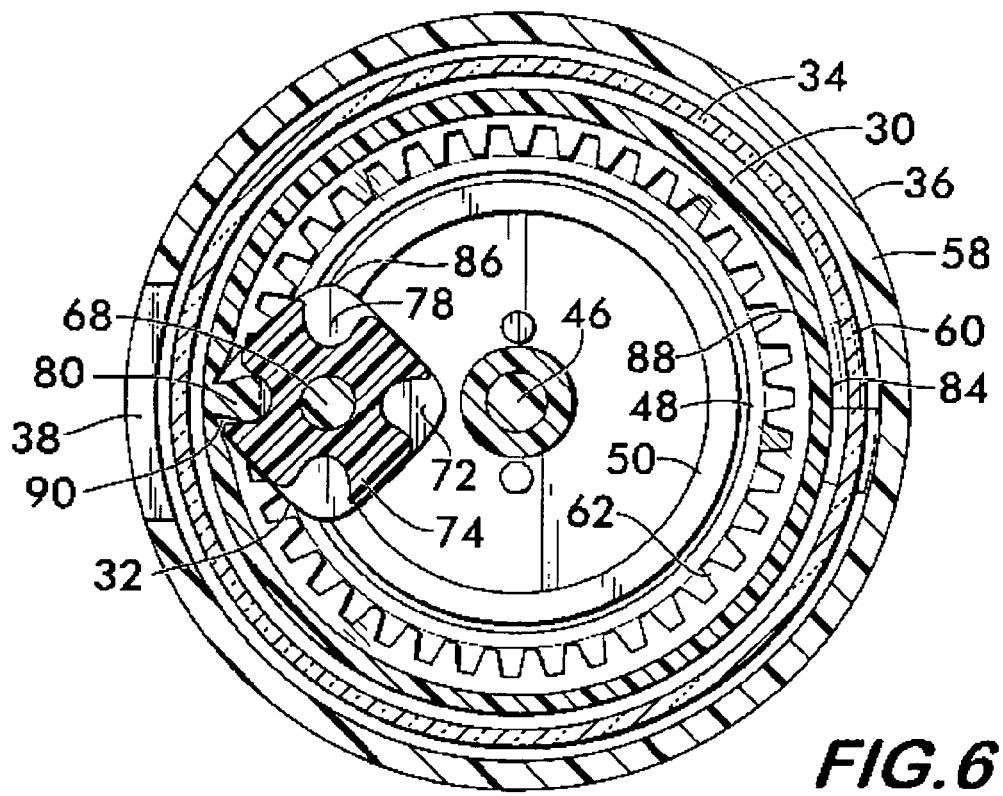
FIG. 6 is a cross-sectional view taken along lines 6-6 in FIG. 4A showing the unit wheel and geneva mechanism in a cooperating position to advance the tens wheel.
Figure 7:
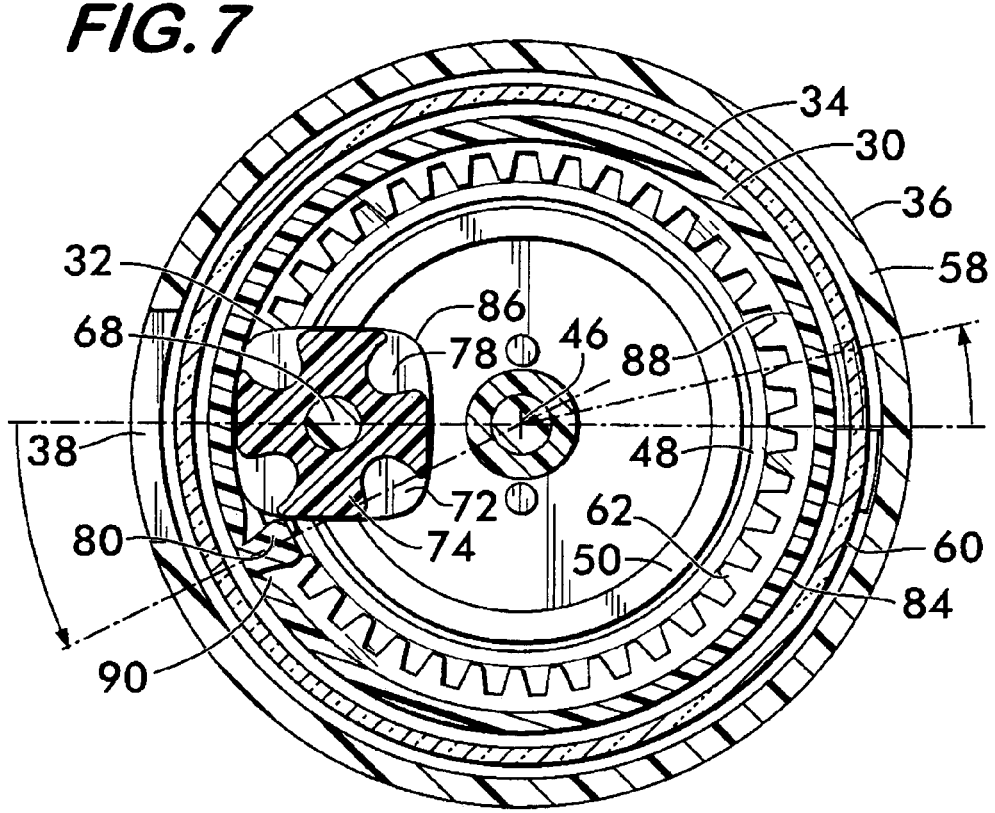
FIG. 7 is a cross-sectional view taken along lines 6-6 in FIG. 4A showing the geneva mechanism in a locked position to prevent advancement of the tens wheel.

A set of inwardly facing gear teeth 62 are positioned circumferentially around the tens wheel 34 above the flange 48. Gear teeth 62 allow the tens wheel 34 to move only when driven by the device and thus prevents freewheeling of the tens wheel 34. As best shown in FIG. 2, slave wheel 32 is mounted on an offset axle 66 extending upwardly from the bottom 44 of the cover 36. Axle 66 is offset from the central axis 46 and thereby provides an offset axis of rotation 68 about which the slave wheel 32 rotates. As shown in FIG. 3, a gear 70 is positioned on one face 72 of the slave wheel 32, the gear 70 meshing with the gear teeth 62 on the tens wheel 34 such that rotation of the slave wheel 32 about the offset axis 68 drives the tens wheel 34 in rotation about the central axis 46 (see also FIG. 8). As shown in FIG. 2, a geneva wheel 74 is positioned on the opposite face 76 of the slave wheel 32. As shown in FIGS. 6 and 7, the geneva wheel 74 has a plurality of receptacles 78, four being shown by way of example. The receptacles 78 are positioned in spaced relation circumferentially around the geneva wheel. Each receptacle is sized and positioned to receive a foot 80 extending downwardly from the unit wheel (see also FIG. 3). The foot 80 engages one of the receptacles 78 once on each complete revolution of the unit wheel 30, and rotates the geneva wheel 74 about the offset axis 68. When the geneva wheel 74 has four receptacles 78, the geneva wheel rotates through an angle of about 90° about the offset axis 68. As shown in FIG. 2, rotation of the geneva wheel 74 causes a corresponding rotation of the gear 70 (since both the geneva wheel 74 and the gear 70 are on opposite faces of the slave wheel 32) which drives the tens wheel 34 in rotation about central axis 46. The geometry and positioning of the geneva wheel 74, gear 70 and the indicia 42 on the tens wheel 34 are such that rotation of the slave wheel 32 positions the next indicia 42 visible within the window 38.

Figure 4:
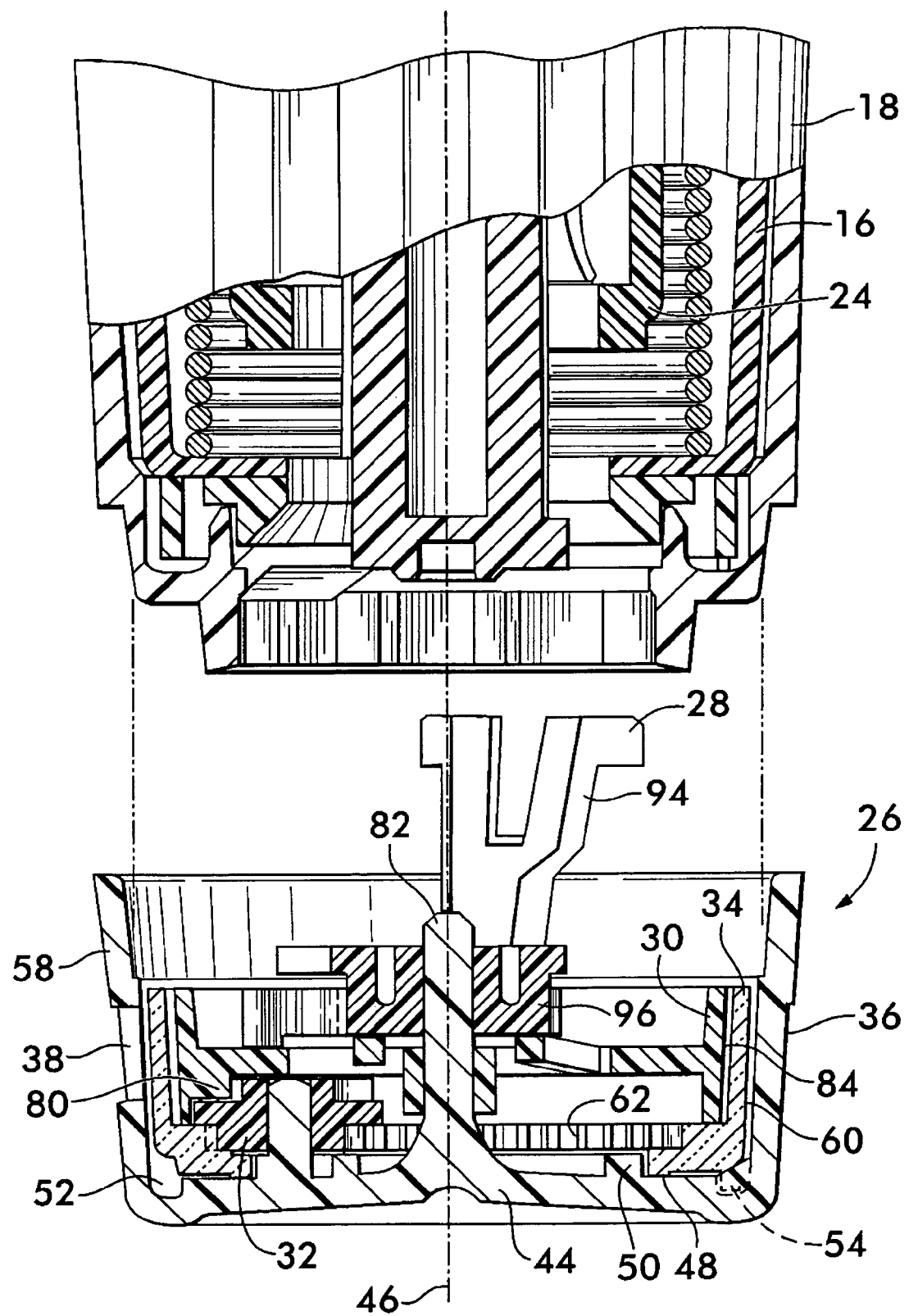
FIG. 4 is an exploded partial sectional view of the counter and the base of the inhaler.
Figure 4A:
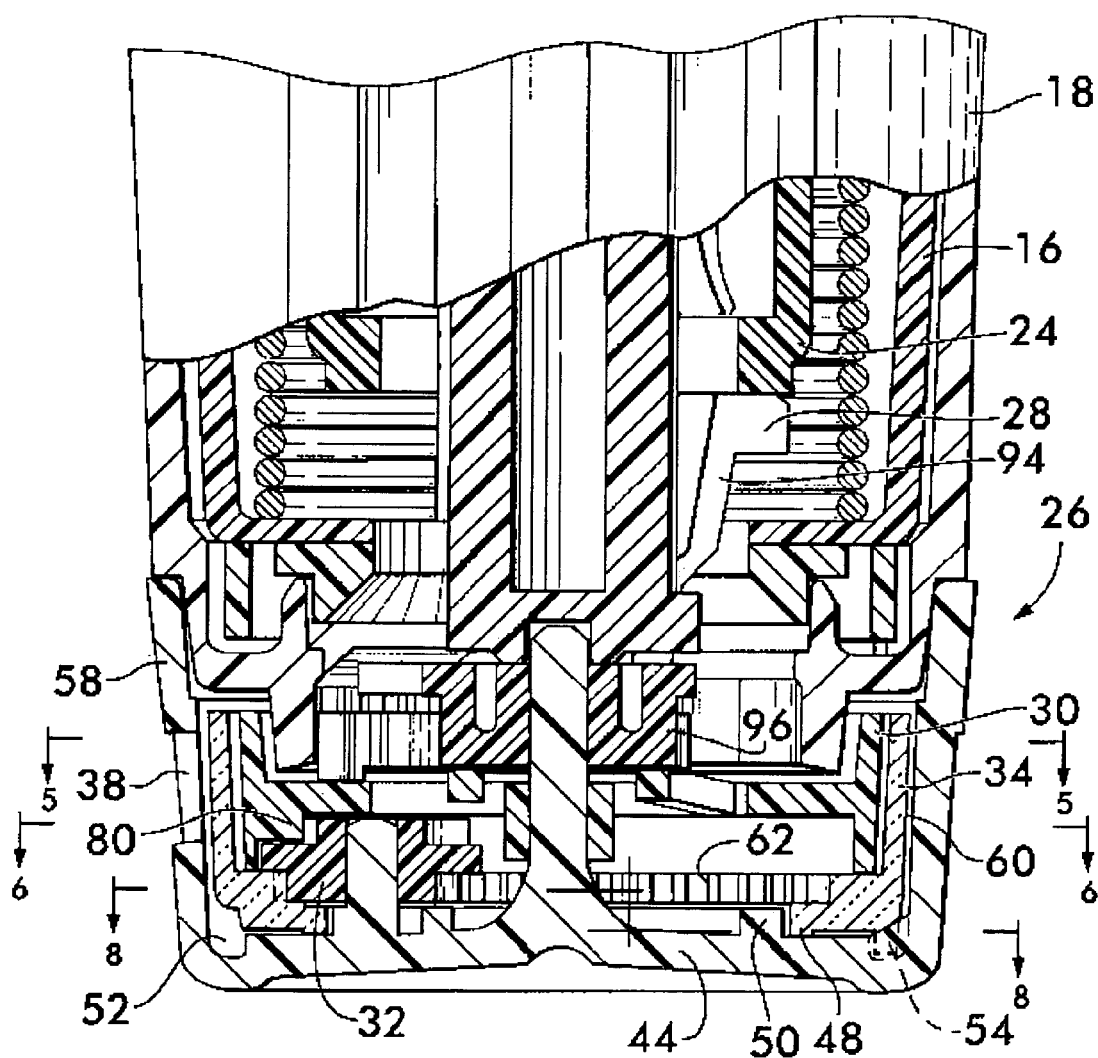
FIG. 4A is a partial sectional view of the counter and the base of the inhaler with the counter assembled and mounted on the inhaler.

As shown in FIG. 2, unit wheel 30 is rotatably mounted on a central axle 82 substantially aligned with the central axis 46 and extending from the bottom 44 of the cover 36. Unit wheel 30 comprises a radially outwardly facing side surface 84 extending circumferentially around and upon which the unit indicia 40 are positioned. Alternatively, the unit wheel may comprise a transparent radial side surface 84 extending circumferentially around, upon which the unit indicia may be positioned on the inward face of said surface so as to still be readable from the outwardly facing surface. As shown in FIGS. 4 and 4A, the unit wheel 30 is nested within the tens wheel 34 such that the outwardly facing side surfaces 60 and 84 are coaxial with and adjacent to one another. The side surface 60 on the tens wheel 34 is transparent, thus, allowing the indicia 40 on the unit wheel behind it to be visible, together with the indicia on the tens wheel 34, through the window 38. The unit indicia 40 are positioned and spaced around side surface 84 so as to align to the right side of the window 38. Thus, together, the tens indicia 42 on the tens wheel 34 and the unit indicia 40 on the unit wheel 30 are visible together in the window 38 to show the number of doses that can still be delivered before the device is considered empty or doses already dispensed from the medicament reservoir 16. Positioning the foot 80 on the unit wheel 30 and the gear teeth 62 on the tens wheel 34 is the preferred configuration, although other configurations, for example, having two or more feet on the unit wheel, altering the ratio of the size of the slave wheel to the master wheel and having a plurality of receptacles, are also feasible.

As shown in FIGS. 2, 6 and 7, slave wheel 32 has a plurality of lobes 86 positioned between the gear 70 and the geneva wheel 74. The lobes 86 extend radially outwardly and are arranged in spaced relation circumferentially about the slave wheel 32, each lobe 86 being positioned next to a corresponding receptacle 78 of the geneva wheel 74. In the example shown, there are four lobes 86 positioned next to corresponding receptacles 78. Lobes 86 engage an inwardly facing circumferential surface 88 on the unit wheel 30. Engagement of two adjacent lobes 86 with the surface 88 prevents rotation of the slave wheel 32 as the unit wheel 30 rotates and hence also prevents rotation of the tens wheel 34. However, there is a notch 90 positioned within the surface 88 adjacent to the foot 80. When the foot 80 engages a receptacle 78 on the geneva wheel 74 as shown in FIG. 6, the lobe 86 adjacent to the receptacle 78 is received within the notch 90 in the circumferential surface 88 of the unit wheel 30. The notch 90 provides clearance between the lobe 86 and the circumferential surface 88, allowing the slave wheel 32 to rotate, thereby rotating the tens wheel 34. After the foot 80 has disengaged from the receptacle 78 as depicted in FIG. 7 and is no longer rotating the slave wheel 32, the next pair of adjacent lobes 86 then align with the circumferential surface 88, thereby, again preventing rotation of the slave wheel until the foot 80 on the unit wheel 30 again engages the next receptacle 78 aligned with the next lobe 86 on the geneva wheel 74.

As shown in FIG. 2, the unit wheel 30 is driven by coupling 28 which couples the motion of the air channel assembly 14 to the counter 26. Coupling 28 has a plurality of legs 94 which extend from the counter 26 into the barrel 18 and engage tabs 111 on the mandrel 24 (not shown) of the air channel assembly 14. Legs 94 are arranged in spaced relation to one another so as to provide for lost motion between the mandrel 24 (not shown) and the coupling 28. The lost motion allows for the large rotational motion of the air channel assembly 14 relative to the drive sub-assembly needed to actuate the inhaler, yet also provides a reduced rotational motion of the air channel assembly 14 relative to the counter 26 needed to actuate the counter. Legs 94 are flexible and, thus, may be resiliently bent to facilitate assembly of the counter onto the inhaler by allowing the legs to flex and be inserted into barrel 18.

Figure 5:
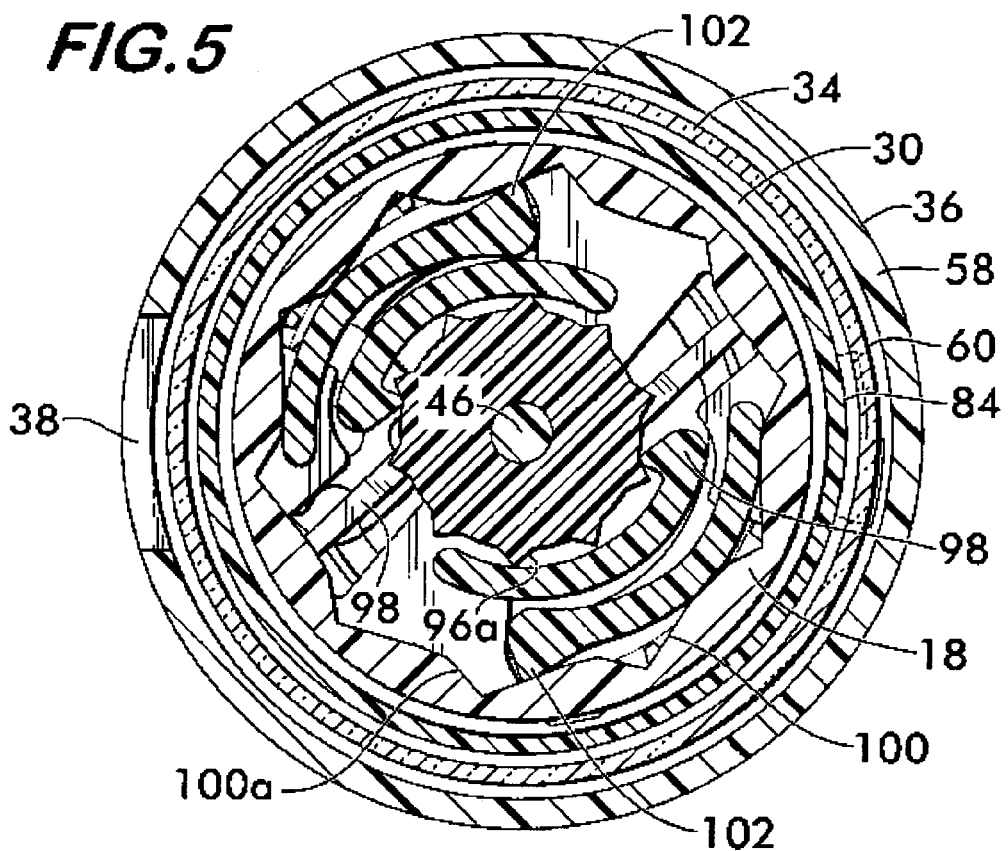
FIG. 5 is a cross-sectional view taken along lines 5-5 in FIG. 4A.

Mounted on the coupling 28 opposite to the legs 94 is a ratchet 96 which engages pawls 98 on the unit wheel 30 (see also FIG. 5). Thus motion of the air channel assembly 14 relative to the barrel 18 as the inhaler is actuated is transmitted from the mandrel 24 (not shown) to the unit wheel 30 by means of the legs 94, the ratchet 96 and the pawls 98 on the unit wheel 30. The ratchet and pawl are used to move the unit wheel only in one direction to decrement (or increment) the counter for each actuation. As described in detail below, actuation of the inhaler 10 requires a reciprocal motion of the air channel assembly 14 relative to the barrel 18, and the reciprocal motion must be converted to unidirectional motion of the counter 26, and this is effected by means of the ratchet 96 and pawls 98. The position of the ratchet 96 on the coupling 28 and pawls 98 on the unit wheel 30 are preferred for ease of manufacture but could easily be reversed and achieve the same desired effect. By keeping both sets of pawls 98 on the same part, variations between the arms in the inhaler device is negated, thus providing a more consistent torque balance.

As shown in FIG. 3, a second ratchet 100 is positioned on the end of barrel 18. As shown in FIG. 5, the ratchet 100 faces radially inwardly to engage pawls 102 which are mounted on the unit wheel 30 and face outwardly to engage the ratchet 100. Ratchet 100 and pawls 102 work in cooperation with ratchet 96 and pawls 98 to prevent retrograde motion of the unit wheel when it is actuated by the reciprocal motion of the air channel assembly 14 relative to the barrel 18. The cooperation of the ratchets and pawls is described in detail below in the description of counter operation. Unidirectional motion of the unit wheel is ensured by proper design of the ratchet angles and relative panel lengths of the ratchets 96 and 100 and pawls 98.

As illustrated in FIG. 3, unit wheel 30 also has a plurality of cantilevered fingers 104 which extend upwardly from the unit wheel and engage the coupling 28. The fingers 104 act as springs to bias the components of the counter 26 against the bottom 44 of cover 36 and the fingers 104 also bias the coupling 28 against the mandrel 24 (not shown). When compressed against the coupling 28, the unit wheel 30 is biased against the tens wheel 34, keeping the slave wheel 32 properly positioned and engaged with the unit and tens wheels. The biasing action of the fingers 104 also keeps the tens wheel 34 properly seated on the bottom 44 and the flange 48 firmly engaged with the raised boss 50 so as to generally ensure smooth operation of the counter and also help prevent powdered medicament from contaminating the counter mechanism.

It is preferred to make the inhaler and counter from plastic materials for cost effective manufacture by injection molding. For example, the barrel 18, cover 26, and cap 12 may be polypropylene, the tens wheel 34 may be polycarbonate, the slave wheel 32 may be polybutylene teraphthalate, while the unit wheel is preferably polycarbonate, the coupling may be polybutylene terephthalate, and the air channel assembly is predominantly made of an acetal copolymer such as Hostaform®.

The term "medicament" as used herein is intended to encompass the presently available pharmaceutically active drugs used therapeutically and further encompasses future developed therapeutically effective drugs that can be administered by the intrapulmonary route. Drugs may be selected from, for example, analgesics, e.g. codeine, dihydromorphine, ergotamine, fentanyl or morphine, anginal preparations, e.g. diltiazem; antiallergics, e.g. cromoglycate, ketotifen or nedocromil; antiinfectives e.g. cephalosporins, penicillins, streptomycin, sulphonamides, tetracyclines pentamidine, and Neuraminidase Inhibitors; antihistamines, e.g. mnethapyfilene; antitussives, e.g. noscapine; beta-adrenergics that include bronchodilators such as ephedrine, adrenaline, fenoterol, forinoterol, isoprenaline, phenylephrine, phenylpropanolamine, reproterol, rimiterol, isoetharine, tulobuterol, orciprenaline, or (−)-4-amino-3,5-dichloro-.alpha.-[[[6-[2-(2-pyridinyl)ethoxy]hexyl]-amino]methyl]benzenemethanol, epinephrine (Primatene), formoterol (Foradil), isoproterenol (Isuprel), isoetharine (Bronkosol), metaproterenol (Alupent, Metaprel), albuterol (Proventil, Ventolin), terbutaline (Bricanyl, Brethine), bitolterol (Tornalate), pirbuterol (Maxair), salmeterol (Serevent), salmeterol+fluticasone combination (Advair Diskus), and albuterol+atrovent combination (Combivent); sodium channel blockers such as amiloride, anticholinergics e.g. ipratropium, atropine or oxftropium; hormones, e.g. cortisone, hydrocordisone or prednisolone; and therapeutic proteins and peptides, e.g. insulin or glucagon; anti-inflammatory drugs used in connection with the treatment of respiratory diseases include steroids such as ciclesonide beclomethasone dipropionate (Vanceril, Beclovent), budesonide (Pulmicort), dexamethasone, flunisolide (Aerobid), fluticasone (Flovent), salmeterol+fluticasone combination (Advair Diskus), and triamcinolone acetonide (Azmacort), and Mediator-release inhibitors such as cromolyn sodium (Intal), and nedocromil sodium (Tilade); leukotrine (LT) inhibitors, vasoactive intestinal peptide (VIP), tachykinin antagonists, bradykinin antagonists, endothelin antagonists, heparin furosemide, anti-adhesion molecules, cytokine modulators, biologically active endonucleases, recombinant human (rh) DNase compounds, alpha-antitrypsin and disodium cromoglycate (DSCG); and lung surfactants such as lipid-containing compositions as described in TONGE et. Al, WO 99/09955; Pulmonary surfactants as described in Devendra et. al, Respir Res 2002, 3:19; Infasurf® available from ONY; Curosurf® available from Dey Laboratories; Exosurf® by Glaxo Wellcome; Survanta available from Abbot; and Surfaxin® lung surfactant available from Discovery Laboratories.

The term "intermittent drive transfer mechanism" as used herein means a mechanism that intermittently transfers the drive from one element to another via a drive transfer wheel. An example of such a mechanism is a geneva mechanism.

The term "drive transfer wheel" as used herein means a wheel capable of intermittently transferring a drive from one element to another. Examples of a drive transfer wheel include a geneva wheel, a star drive wheel or a maltese cross wheel. Preferably, the drive transfer wheel is a geneva wheel.

Inhaler and Counter Operation

Operation of the inhaler 10 is described in detail in Drought N., U.S. Pat. No. 5,678,538, which is hereby incorporated by reference in its entirety. Provided below is a simplified explanation of inhaler operation as it relates to the counter 26.

With reference to FIGS. 1 and 2, to administer a metered dose of powdered medicament, a user grasps the barrel 18 in one hand and the dust cap 12 in the other. The cap 12 and barrel 18 are rotated relatively to one another through an angle of about 105° about the central axis 46 with the cap 12 rotating clockwise and the barrel 18 counterclockwise when viewed from the cap end of the inhaler 10. Cap 12 has a tab 106 which engages a notch 108 in collar 22, causing the entire air channel assembly 14 to rotate clockwise along with the cap 12. The cap 12 and barrel 18 are then relatively rotated in the reverse direction through the same angle. The reciprocal rotation of the cap 12 and air channel assembly 14 causes a metered dose of powdered medicament to be scraped from the reservoir 16 and deposited in the air channel assembly 14. The user removes the cap 12, places his or her lips to the mouthpiece 20 and inhales. The medicament becomes entrained in an air stream drawn through the mouthpiece 20 and is drawn into the mouth, trachea and lungs of the user where it is absorbed.

The relative rotation between the barrel 18 and the air channel assembly 14 is used to actuate the counter 26. By way of example only, a decrementing counter, which counts down and indicates the number of doses that can still be delivered before the device is considered empty, is described below, it being understood that an incrementing counter, which counts upward and indicates the number of doses administered, functions in essentially the same way as the decrementing counter. Changing a decrementing counter to an incrementing counter is easily carried out by changing the arrangement of the printed numbers on the tens and unit wheels. References to clockwise and counterclockwise rotations which follow are defined as if viewed from the dust cap 12 of the inhaler along central axis 46.

The initial clockwise rotation of the air channel assembly 14 through about 105° is transmitted to the unit wheel 30 by the coupling 28. Legs 94 engage the mandrel 24 (not shown) on the air channel assembly to transmit the motion. There is lost motion between the legs 94 and the mandrel 24 over an angle of about 56.5°. After this point in the rotation, the mandrel contacts the legs and rotates the coupling 28 through an angle of about 48.5° clockwise. As shown in FIG. 5, ratchet 96 on the coupling is rotated clockwise relatively to pawls 98 on the unit wheel, the pawls 98 slipping over the ratchet teeth 96*a* and clicking into place on the other side of the teeth, ready to move the unit wheel 30 upon the reverse rotation of the air channel assembly 14. The unit wheel 30 is prevented from rotating clockwise as the pawls 98 engage and slip over the teeth 96*a* by the second ratchet 100 located in barrel 18, engaged by outer pawls 102 on the unit wheel 30. Note that the pawls 98 are stressed in bending only during motion of the coupling 28 relative to the unit wheel. At all other times, the pawls remain unstressed and, thus, will not take on a permanent set which could adversely affect the ratcheting action of the mechanism.

The user then turns the cap 12 relative to the barrel 18 through a counterclockwise rotation of about 105°, loading a dose of medicament into the air channel assembly 14 and also causing the counter to decrement one unit. Again, there is lost motion between the mandrel 24 and the coupling 28 over about 56.5° of the rotation. After this point, the mandrel 24 causes the coupling 28 to rotate counterclockwise through an angle of about 48.5°. During this rotation, ratchet 96 (see FIG. 5), rotating counterclockwise, engages pawls 98 on the unit wheel 30 and rotates the unit wheel counterclockwise about the central axis 46 so that the next lower value of the indicia 40 is displayed in the window 38. There is lost motion between the ratchet 96 and pawls 98 such that the unit wheel 30 is rotated though an angle of 36°, thus, providing ten decrements of the unit wheel over a complete revolution through 360°. The lost motion is obtained by appropriate spacing of the ratchet teeth 96*a*. Upon counter clockwise rotation of the unit wheel 30, the pawls 102 slip over the ratchet teeth 100*a* to engage the next teeth and lock the unit wheel in place until the next dose is loaded by the clockwise and counterclockwise rotation of the air channel assembly 14 relative to the barrel 18.

Figure 8:
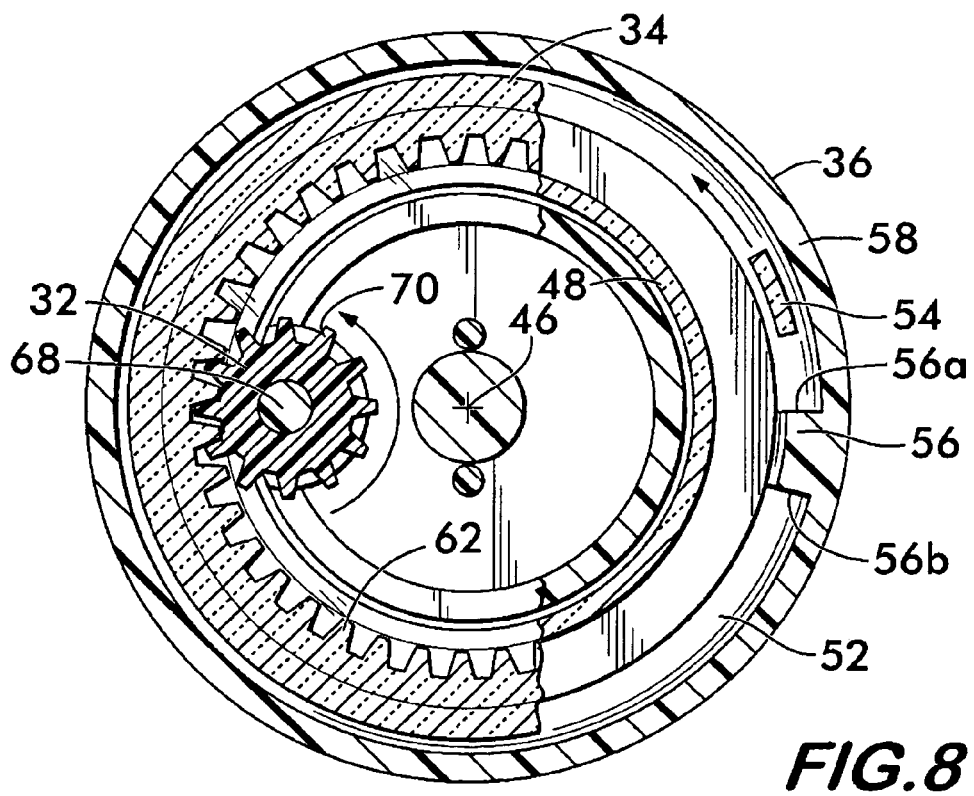
FIG. 8 is a cross-sectional view taken along lines 8-8 in FIG. 4A.

On each tenth decrement of the unit wheel 30, the foot 80 extending therefrom engages one of the receptacles 78 on the geneva wheel 74 as shown in FIG. 6. Counterclockwise motion of the unit wheel 30 through the tenth decrement causes counterclockwise rotation of the slave wheel 32 about the offset axis 68. Rotation of the slave wheel 32 is permitted because the lobe 86 adjacent to the receptacle 78, which normally engages the surface 88 of the unit wheel to prevent rotation, is received within the notch 90 in the surface 88, providing clearance allowing the slave wheel to rotate. Over the 36° of rotation of the unit wheel 30, the first and last 3° are lost motion relative to the slave wheel 32, and the middle 30° rotates the slave wheel through 90°. The purpose of the lost motion is to ensure that immediately before and after the tens stroke, the foot is not engaged with the receptacle, which means that the geneva mechanism cannot be driven by the user driving the tens wheel. As shown in FIG. 8, gear 70 on the slave wheel 32 also rotates counterclockwise through 90°, its teeth engaging the gear teeth 62 on the tens wheel 34, and causing a counterclockwise rotation of the tens wheel 34 about the central axis 46 to bring the next lower indicia 42, indicating tens of doses, into view within the window 38. Indicia 40 on the unit wheel 30 are visible through the transparent tens wheel 34 and align with the indicia 42 on the tens wheel and together indicate the number of doses that can still be delivered before the device is considered empty. The gear ratio between gear 70 and the tens wheel 34 is designed to move the tens wheel in proportion to the number of divisions, indicated by the indicia 42, on the tens wheel 34. For example, a dose counter having 120 doses will require 13 divisions, corresponding to indicia from 1-12 and a blank space indicating zero, positioned on the tens wheel 34. Thus, with each complete revolution of the unit wheel (with ten divisions numbered 0-9), the tens wheel 34 should move through an angle of about 27.7° (¹/₁₃ of a complete revolution). Note that this rotation must be achieved by a 90° rotation of the gear 70. A ratio of about 3.25 to 1 between the tens wheel 34 and the gear 70 will cause the desired rotation of the tens wheel 34. As best shown in FIG. 3, it is advantageous to provide colored indicators 110 on the tens wheel 34 positioned near the low numbered indicia 42 to provide a readily visible warning that few doses remain in the inhaler.

A complete revolution of the tens wheel 34 is prevented by the engagement of tab 54 with the stop block 56 positioned within the circular groove 52 in the bottom 44 of cover 36 (see FIGS. 2 and 8). As shown in FIG. 8, tab 54 is initially positioned adjacent to one side 56a of the stop block 56 (the position corresponding to the maximum indicia 42 being aligned within window 38) and initially moves counterclockwise away from the stop block as the tens wheel 34 rotates. When fewer than ten doses remain within the inhaler, the space on the tens wheel 34 aligned within window 38 is blank, displaying one of the colored indicators 110, and the tab 54 is engaged with the opposite side 56b of the stop block 56. This prevents any additional rotation of the tens wheel 34 after the final ten decrements of the unit wheel, thus, preventing the counter 26 from resetting itself by aligning the maximum tens indicia 42 within the window, which would occur if the tens wheel 34 were permitted to revolve beyond the complete revolution. However, even though the counter indicates no doses remaining, there may still be sufficient medicament in the reservoir to provide additional therapeutic doses to the user. The inhaler is designed so that the counter 26 may be overridden to administer any additional doses remaining after zero doses are indicated. Override of the counter is possible due to the design of ratchet 96 and pawls 98. When the tens wheel 34 is prevented from turning, and upon application of sufficient torque by the user turning the cap 12, the pawls 98 will slip over the ratchet teeth 96a as the coupling 28 moves in the counterclockwise direction, thereby allowing a medicament dose to be loaded into the air channel assembly without actuating the counter 26. Normally, the pawls 98 engage the teeth 96a of ratchet 96 when the ratchet turns in the counterclockwise direction to actuate the counter 26. However, the pawls 98 are sufficiently flexible such that they will disengage from the ratchet rather than jam the entire inhaler mechanism when sufficient torque is applied and the tens wheel 34 is blocked by the stop block 56.

The inhaler and counter according to the invention provides a compact, inexpensive and reliable means for administering measured doses of a powdered medicament, while knowing with a significant degree of precision how many doses are remaining in the inhaler at any given time and when an inhaler should be replaced with a new one.

One skilled in the art will readily appreciate that the present invention is well adapted to carry out the objects of the invention, and obtain the ends and advantages mentioned, as well as those inherent therein. The inhaler, counter, slave wheel, methods, and articles of manufacture described herein are presented as representative of the preferred embodiments, or intended to be exemplary and not intended as limitations on the scope of the present invention.

What is claimed is:

1. A dry powder inhaler for administering a dose of a medicament, said inhaler comprising:
   a reservoir holding said medicament;
   an air channel assembly engaged with, and movable relatively to, said reservoir for receiving said dose of medicament upon said relative motion; and
   a counter for counting a number of doses dispensed from said reservoir or that can still be delivered before the inhaler is considered empty said counter comprising a first indicator member which moves one increment in response to said relative motion, and a second indicator member which moves intermittently in response to motion of said first indicator member, a rotatory intermittent drive transfer mechanism being positioned between and engageable with said first and second indicator members, said first indicator member driving said rotatory intermittent drive transfer mechanism, said rotatory intermittent drive transfer mechanism driving said second indicator member intermittently upon motion of said first indicator member, said first and second indicator members having indicia thereon for displaying the number of said doses dispensed from said reservoir or that can still be delivered before the inhaler is considered empty.

2. The inhaler according to claim 1 adapted to administer said medicament orally.

3. The inhaler according to claim 1, wherein said reservoir is arranged circumferentially around a central axis, said air channel assembly being positioned coaxially with said reservoir and rotatably movable about said axis relatively thereto, said first indicator member and said second indicator member also being positioned coaxially with said reservoir and rotatably movable about said axis for counting said doses dispensed from said reservoir or doses that can still be delivered before the inhaler is considered empty.

4. The inhaler according to claim 1, further comprising a ratchet and pawl for connecting said first indicator member to said air channel assembly for motion of said first indicator member in response to motion of said air channel assembly relatively to said reservoir, said ratchet being mounted on one of said first indicator member and said air channel assembly and rotatable about said axis therewith, said pawl being mounted on the other of said first indicator member and said air channel assembly and engaging said ratchet for causing rotational motion of said first indicator member only in one direction about said axis.

5. The inhaler according to claim 4, wherein said pawl is mounted on said first indicator member and said ratchet is mounted on said air channel assembly.

6. The inhaler according to claim 4, further comprising a coupling positioned between said first indicator member and said air channel assembly, one end of said coupling interfacing with said first indicator member and comprising one of said ratchet and said pawl, the other end of said coupling having a plurality of legs extending therefrom for engaging said air channel assembly, said coupling transmitting relative motion of said air channel assembly to said counter for moving said first indicator member.

7. The inhaler according to claim 6, wherein said ratchet is mounted on said coupling and said pawl is mounted on said first indicator member, said ratchet engaging said pawl for rotating said first indicator member about said axis in response to motion of said air channel assembly.

8. The inhaler according to claim 1, wherein said first indicator member and second indicator member rotate in the same direction during operation.

9. The inhaler according to claim 1, wherein said first indicator member has a first surface on which said indicia appear, said first surface facing radially outwardly from said axis, said second indicator member has a second surface on which said indicia appear, said second surface being transparent and facing radially outwardly from said axis, said first indicator member being nested within said second indicator member, said indicia on said first indicator member aligning with said indicia on said second indicator member and being visible therethrough to display the number of said doses dispensed from said reservoir or that can still be delivered before the inhaler is considered empty.

10. The inhaler according to claim 1, wherein said rotatory intermittent drive transfer mechanism comprises a slave wheel rotatable about an offset axis offset from said central axis and substantially parallel thereto, said slave wheel having a drive transfer wheel on one face and a gear on an opposite face.

11. The inhaler according to claim 1, wherein said first indicator member has a foot extending therefrom for engaging said drive transfer wheel, the second indicator member having gear teeth arranged circumferentially therearound for meshing with said gear on said opposite face, upon rotation of said first indicator member, said first indicator member engaging and rotating said slave wheel, said slave wheel engaging and rotating said second indicator member intermittently.

12. The inhaler according to claim 11, wherein said foot is mounted on said first indicator member and said gear teeth are positioned on said second indicator member.

13. The inhaler according to claim 1, wherein said first indicator member comprises a unit wheel and said second indicator member comprises a tens wheel, said second indicator member moving once for every ten movements of said unit wheel.

14. The inhaler according to claim 1, further comprising a third, and optionally a fourth, indicator member.

15. The inhaler according to claim 1, further comprising a cover mounted on an end of said inhaler opposite said air channel assembly, said cover comprising a bottom and an outwardly facing sidewall extending circumferentially around said bottom, said second indicator member (e.g. a tens wheel) having a projection mounted thereon, said cover bottom comprising a stop block positioned for engaging said projection and preventing a full rotation of said second indicator member (e.g. a tens wheel) relatively to said cover.

16. A dry powder inhaler for administering a dose of a medicament, said inhaler comprising:
   a reservoir holding said medicament;
   an air channel assembly engaged with and movable relatively to said reservoir for receiving said dose of medicament upon said relative motion; and
   a counter for counting a number of doses dispensed from said reservoir or that can still be delivered before the inhaler is considered empty, said counter comprising a coupling engaging said air channel assembly and a first indicator member and imparting rotation to said first indicator member on rotation of said air channel assembly, a second indicator member which rotates intermittently in response to motion of said first indicator member, one of said indicator members having a transparent side surface facing outwardly, the other of said indicator members being nested coaxially within the one wheel and having an inwardly and outwardly facing side surface, said outwardly facing side surface positioned adjacent to the transparent side surface, said surfaces having indicia thereon for displaying the number of said doses dispensed from said reservoir or that can still be delivered before the inhaler is considered empty.

17. The inhaler according to claim 16 adapted to administer said medicament orally.

18. The inhaler according to claim 16, further comprising a rotatory intermittent drive transfer mechanism positioned between and engageable with said first indicator member and said second indicator member, said first indicator member driving said rotatory intermittent drive transfer mechanism, said rotatory intermittent drive transfer mechanism driving said second indicator member intermittently upon motion of said first indicator member.

19. The inhaler according to claim 18, wherein said rotatory intermittent drive transfer mechanism comprises a slave wheel rotatable about an offset axis offset from said central axis and substantially parallel thereto, said slave wheel having a drive transfer wheel on one face and a gear on an opposite face.

20. The inhaler according to claim 19, wherein said first indicator member has a foot extending therefrom for engaging said drive transfer wheel, the second indicator member having gear teeth arranged circumferentially therearound for meshing with said gear on said opposite face, upon rotation of said first indicator member, said first indicator member engaging and rotating said slave wheel, said slave wheel engaging and rotating said second indicator member intermittently.

21. The inhaler according to claim 20, wherein said foot is mounted on said first indicator member and said gear teeth are positioned on said second indicator member.

22. The inhaler according to claim 16, wherein said second indicator member moves one increment for every ten increments of said first indicator member.

23. The inhaler according to claim 16, wherein said reservoir is arranged circumferentially around a central axis, said air channel assembly being positioned coaxially with said reservoir and rotatably movable about said central axis relatively thereto, said first and said second indicator members also being positioned coaxially with said reservoir and rotatably movable about said central axis for counting said doses dispensed from said reservoir or that can still be delivered before the inhaler is considered empty.

24. The inhaler according to claim 16, wherein said first indicator member is nested coaxially within said second indicator member, said second indicator member having said transparent side surface.

25. The inhaler according to claim 16, further comprising a ratchet and pawl for rotating said first indicator member in response to the rotation of said air channel assembly and said coupling, said ratchet being mounted on one of said first indicator member and said coupling, and rotatable about said central axis therewith, said pawl being mounted on the other of said first indicator member and said coupling and engaging said ratchet for causing rotational motion of said first indicator member only in one direction about said central axis.

26. The inhaler according to claim 25, wherein said pawl is mounted on said first indicator member.

27. The inhaler according to claim 16, wherein said ratchet comprises a plurality of teeth positioned circumferentially around said axis in spaced relation to one another, said spaced relation between said teeth being predetermined to allow lost motion between said coupling and said first indicator member.

28. The inhaler according to claim 16, further comprising a cover mounted on an end of said inhaler opposite said air channel assembly, said cover comprising a bottom and an outwardly facing sidewall extending circumferentially around said bottom, said second indicator member having a projection mounted thereon, said cover bottom comprising a stop block positioned for engaging said projection and preventing a full rotation of said second indicator member relatively to said cover.

29. The inhaler according to claim 16, wherein said first indicator member comprises a unit wheel and said second indicator member comprises a tens wheel.

30. The inhaler according to claim 16, wherein said first indicator member and second indicator member rotate in the same direction during operation.

31. The inhaler according to claim 16, further comprising a third and optionally a fourth indicator member.

32. A method f or treating a respiratory disorder in a patient comprising the step of inhaling by a patient in need of such treatment, a therapeutically effective amount of a medicament using the dry powder inhaler of claim 1.

33. The method of claim 32, wherein the respiratory disorder is selected from the group consisting of asthma, chronic obstructive lung disease, cystic fibrosis, and pneumonia.

34. The method of claim 32, wherein the medicament is selected from the group consisting of a bronchodilator, an antihistamine, a lung surfactant, an antiviral agent, a corticosteroid, an anti-inflammatory agent, an anti-cholinergic, and an antibiotic.

35. A method for treating a respiratory disorder in a patient comprising the steps of:
providing the dry powder inhaler of claim 1;
actuating the medicament into the patient;
causing the counter to indicate the number of metered dosages dispensed from said reservoir or that can still be delivered before the inhaler is considered empty.

36. A method of administering a dose of a medicament to a patient in need thereof, from a dry powder inhaler, said method comprising the steps of:
providing a reservoir holding said medicament, said reservoir fits coaxially within a barrel, and a mandrel of an air channel assembly fits coaxially within the reservoir;
providing an air channel assembly comprising a mouthpiece, or nasalpiece, a collar and a mandrel, said air channel assembly engaged with, and movable relatively to, said reservoir for receiving said dose of medicament upon said relative motion;
providing a counter for counting a number of doses dispensed from said reservoir or that can still be delivered before the inhaler is considered empty, said counter comprising a first indicator member which moves one increment in response to said relative motion, and a second indicator member which moves intermittently in response to motion of said first indicator member;
providing a rotatory intermittent drive transfer mechanism positioned between and engageable with said first and second indicator members, said first indicator member driving said rotatory intermittent drive transfer mechanism, said rotatory intermittent drive transfer mechanism driving said second indicator member intermittently upon motion of said first indicator member, said first and second indicator members having indicia thereon for displaying the number of said doses dispensed from said reservoir or that can still be delivered before the inhaler is considered empty; and
rotating the cap and barrel relative to one another through an angle of about 105° about the central axis with the cap rotating clockwise and the barrel counterclockwise when viewed from the cap end of the inhaler;
engaging a tab in said cap which engages a notch in the collar, causing the entire air channel assembly to rotate clockwise along with the cap;
then rotating the cap and barrel in the reverse direction through the same angle;
reciprocally rotating the cap and air channel assembly causing a metered dose of powdered medicament to be scraped from the reservoir and deposited in the air channel assembly;
removing the cap;
placing the patient's lips or nasal passage on the mouthpiece, or nasalpiece; and inhaling.

37. A device for administering a dose of a medicament to a patient in need thereof, comprising:
an air channel assembly comprising a mandrel;
a counter comprising a coupling, a first indicator member, a slave wheel, a second indicator member and a cover in which the first indicator member, slave wheel and second indicator member are rotatably mounted, wherein the coupling has a plurality of legs which extend from the counter into the barrel and engage tabs on the mandrel of the air channel assembly, wherein the legs are arranged in spaced relation to one another so as to provide for lost motion between the mandrel and the coupling;
wherein on the coupling opposite to the legs is mounted a ratchet which engages inner pawls on the first indicator member; and
a second ratchet positioned on the end of the barrel;
wherein the second ratchet faces radially inwardly to engage outer pawls which are mounted on the first indicator member.

38. The device according to claim 37, wherein the air channel assembly is capable of forward rotation through about 105°, said rotation is transmitted to the first indicator member by the coupling, wherein the legs engage the mandrel on the air channel assembly to transmit the motion, wherein the forward rotation of the coupling causes the ratchet on the coupling to forward rotate relatively to pawls on the first indicator member, resulting in the pawls slipping over the ratchet teeth and being positioned on the other side of the teeth, so that the position of the pawls and teeth are such that they are ready to move the first indicator member upon the reverse rotation of the air channel assembly.

39. The device according to claim 38, wherein the first indicator member is prevented from forward rotating, when the pawls engage and slip over the teeth, by the second ratchet located in the barrel, engaged by outer pawls on the first indicator member.

40. The device according to claim 39, wherein the air channel assembly is capable of reverse rotation through about 105°, causing the loading of a dose of medicament into the air channel assembly; and
causing the counter to indicate the number of metered dosages dispersed from the dry powder inhaler or that can still be delivered before the inhaler is considered empty.

41. The device according to claim 37, wherein said first indicator member comprises a unit wheel and said second indicator member comprises a tens wheel, said second indicator member moving once for every ten movements of said unit wheel.

42. The device according to claim 37, wherein said first indicator member and second indicator member rotate in the same direction during operation.

43. The device according to claim 37, further comprising a third and optionally a fourth indicator member.

44. An article of manufacture, comprising the inhaler according to claim 1 packaged within containing means, and instruction means for using the inhaler.

45. The article according to claim 44, wherein the instructions means is a label or tag attached to the packaging, a printed package insert, or a combination thereof.

46. The article according to claim 44, further comprising a dry powder medication, instruction means for assembly of the inhaler, instruction means for use of the inhaler, or a combination thereof.

47. The inhaler according to claim 2, wherein said reservoir is arranged circumferentially around a central axis, said air channel assembly being positioned coaxially with said reservoir and rotatably movable about said axis relatively thereto, said first indicator member and said second indicator member also being positioned coaxially with said reservoir and rotatably movable about said axis for counting said doses dispensed from said reservoir or doses that can still be delivered before the inhaler is considered empty.

48. The inhaler according to claim 47, further comprising a ratchet and pawl for connecting said first indicator member to said air channel assembly for motion of said first indicator member in response to motion of said air channel assembly relatively to said reservoir, said ratchet being mounted on one of said first indicator member and said air channel assembly and rotatable about said axis therewith, said pawl being mounted on the other of said first indicator member and said air channel assembly and engaging said ratchet for causing rotational motion of said first indicator member only in one direction about said axis.

49. The inhaler according to claim 48, wherein said pawl is mounted on said first indicator member and said ratchet is mounted on said air channel assembly.

50. The inhaler according to claim 49, further comprising a coupling positioned between said first indicator member and said air channel assembly, one end of said coupling interfacing with said first indicator member and comprising one of said ratchet and said pawl, the other end of said coupling having a plurality of legs extending therefrom for engaging said air channel assembly, said coupling transmitting relative motion of said air channel assembly to said counter for moving said first indicator member.

51. The inhaler according to claim 50, wherein said ratchet is mounted on said coupling and said pawl is mounted on said first indicator member, said ratchet engaging said pawl for rotating said first indicator member about said axis in response to motion of said air channel assembly.

52. The inhaler according to claim 51, wherein said first indicator member and second indicator member rotate in the same direction during operation.

53. The inhaler according to claim 52, wherein said rotatory intermittent drive transfer mechanism comprises a slave wheel rotatable about an offset axis offset from said central axis and substantially parallel thereto, said slave wheel having a drive transfer wheel on one face and a gear on an opposite face.

54. The inhaler according to claim 53, wherein said first indicator member has a foot extending therefrom for engaging said drive transfer wheel, the second indicator member having gear teeth arranged circumferentially therearound for meshing with said gear on said opposite face, upon rotation of said first indicator member, said first indicator member engaging and rotating said slave wheel, said slave wheel engaging and rotating said second indicator member intermittently.

55. The inhaler according to claim 54, wherein said foot is mounted on said first indicator member and said gear teeth are positioned on said second indicator member.

56. The inhaler according to claim 55, wherein said first indicator member comprises a unit wheel and said second indicator member comprises a tens wheel, said second indicator member moving once for every ten movements of said unit wheel.

57. The inhaler according to claim 56, further comprising a third, and optionally a fourth, indicator member.

58. The inhaler according to claim 57, further comprising a cover mounted on an end of said inhaler opposite said air channel assembly, said cover comprising a bottom and an outwardly facing sidewall extending circumferentially around said bottom, said second indicator member (e.g. a tens wheel) having a projection mounted thereon, said cover bottom comprising a stop block positioned for engaging said projection and preventing a full rotation of said second indicator member (e.g. a tens wheel) relatively to said cover.

59. The inhaler according to claim 17, further comprising a rotatory intermittent drive transfer mechanism positioned between and engageable with said first indicator member and said second indicator member, said first indicator member driving said rotatory intermittent drive transfer mechanism, said rotatory intermittent drive transfer mechanism driving said second indicator member intermittently upon motion of said first indicator member.

60. The inhaler according to claim 59, wherein said rotatory intermittent drive transfer mechanism comprises a slave wheel rotatable about an offset axis offset from said central axis and substantially parallel thereto, said slave wheel having a drive transfer wheel on one face and a gear on an opposite face.

61. The inhaler according to claim 60, wherein said first indicator member has a foot extending therefrom for engaging said drive transfer wheel, the second indicator member having gear teeth arranged circumferentially therearound for meshing with said gear on said opposite face, upon rotation of said first indicator member, said first indicator member engaging and rotating said slave wheel, said slave wheel engaging and rotating said second indicator member intermittently.

62. The inhaler according to claim 61, wherein said foot is mounted on said first indicator member and said gear teeth are positioned on said second indicator member.

63. The inhaler according to claim 62, wherein said second indicator member moves one increment for every ten increments of said first indicator member.

64. The inhaler according to claim 63, wherein said reservoir is arranged circumferentially around a central axis, said air channel assembly being positioned coaxially with said reservoir and rotatably movable about said central axis relatively thereto, said first and said second indicator members also being positioned coaxially with said reservoir and rotatably movable about said central axis for counting said doses dispensed from said reservoir or that can still be delivered before the inhaler is considered empty.

65. The inhaler according to claim 64, wherein said first indicator member is nested coaxially within said second indicator member, said second indicator member having said transparent side surface.

66. The inhaler according to claim 65, further comprising a ratchet and pawl for rotating said first indicator member in response to the rotation of said air channel assembly and said coupling, said ratchet being mounted on one of said first indicator member and said coupling, and rotatable about said central axis therewith, said pawl being mounted on the other of said first indicator member and said coupling and engaging said ratchet for causing rotational motion of said first indicator member only in one direction about said central axis.

67. The inhaler according to claim 66, wherein said pawl is mounted on said first indicator member.

68. The inhaler according to claim 67, wherein said ratchet comprises a plurality of teeth positioned circumferentially around said axis in spaced relation to one another, said spaced relation between said teeth being predetermined to allow lost motion between said coupling and said first indicator member.

69. The inhaler according to claim 68, further comprising a cover mounted on an end of said inhaler opposite said air channel assembly, said cover comprising a bottom and an outwardly facing sidewall extending circumferentially around said bottom, said second indicator member having a projection mounted thereon, said cover bottom comprising a stop block positioned for engaging said projection and preventing a full rotation of said second indicator member relatively to said cover.

70. The inhaler according to claim 69, wherein said first indicator member comprises a unit wheel and said second indicator member comprises a tens wheel.

71. The inhaler according to claim 70, wherein said first indicator member and second indicator member rotate in the same direction during operation.

72. The inhaler according to claim 71, wherein said first indicator member and second indicator member rotate in the same direction during operation.

73. The device according to claim 40, wherein said first indicator member comprises a unit wheel and said second indicator member comprises a tens wheel, said second indicator member moving once for every ten movements of said unit wheel.

74. The device according to claim 73, wherein said first indicator member and second indicator member rotate in the same direction during operation.

75. The device according to claim 73, further comprising a third and optionally a fourth indicator member.

76. An article of manufacture, comprising the inhaler according to claim 31 packaged within containing means, and instruction means for using the inhaler.

77. The article according to claim 76, wherein the instructions means is a label or tag attached to the packaging, a printed package insert, or a combination thereof.

78. The article according to claim 44, wherein the instructions means is a label or tag attached to the packaging, a printed package insert, or a combination thereof.

79. The inhaler according to claim 52, wherein said first indicator member has a first surface on which said indicia appear, said first surface facing radially outwardly from said axis, said second indicator member has a second surface on which said indicia appear, said second surface being transparent and facing radially outwardly from said axis, said first indicator member being nested within said second indicator member, said indicia on said first indicator member aligning with said indicia on said second indicator member and being visible therethrough to display the number of said doses dispensed from said reservoir or that can still be delivered before the inhaler is considered empty.

* * * * *

UNITED STATES PATENT AND TRADEMARK OFFICE
CERTIFICATE OF CORRECTION

PATENT NO.         : 7,322,352 B2
APPLICATION NO.    : 10/665873
DATED              : January 29, 2008
INVENTOR(S)        : Stephen John Minshull et al.

Page 1 of 1

It is certified that error appears in the above-identified patent and that said Letters Patent is hereby corrected as shown below:

In column 8, line 12, delete "teraphthalate," and insert -- terephthalate, --, therefor.

In column 8, line 28, delete "mnethapyfilene;" and insert -- methapyrilene; --, therefor.

In column 8, line 30, delete "forinoterol," and insert -- formoterol, --, therefor.

In column 8, line 42, delete "oxftropium;" and insert -- oxitropium; --, therefor.

In column 8, line 43, delete "hydrocordisone" and insert -- hydrocortisone --, therefor.

In column 8, line 52, delete "leukotrine" and insert -- leukotriene --, therefor.

In column 15, line 6, in claim 32, delete "f or" and insert -- for --, therefor.

In column 20, line 4, in claim 75, delete "claim 73," and insert -- claim 74, --, therefor.

Signed and Sealed this
Twelfth Day of April, 2011

David J. Kappos
*Director of the United States Patent and Trademark Office*